(12) United States Patent
Marik et al.

(10) Patent No.: US 9,271,758 B2
(45) Date of Patent: Mar. 1, 2016

(54) BONE FASTENER AND METHODS OF USE

(75) Inventors: Gregory Marik, Collierville, TN (US); Trevor Seck, Memphis, TN (US)

(73) Assignee: Warsaw, Orthopedic, Inc., Warsaw, IN (US)

( * ) Notice: Subject to any disclaimer, the term of this patent is extended or adjusted under 35 U.S.C. 154(b) by 518 days.

(21) Appl. No.: 13/597,022

(22) Filed: Aug. 28, 2012

(65) Prior Publication Data

US 2014/0066991 A1     Mar. 6, 2014

(51) Int. Cl.
*A61B 17/86*     (2006.01)
*A61B 17/70*     (2006.01)

(52) U.S. Cl.
CPC ......... *A61B 17/7032* (2013.01); *A61B 17/8625* (2013.01); *A61B 17/8685* (2013.01); *A61B 17/8695* (2013.01)

(58) Field of Classification Search
CPC ............. A61B 17/8685; A61B 17/864; A61B 17/8625; A61B 17/7037; A61B 17/7032; A61B 17/863; A61B 17/686; A61B 17/8605; A61B 17/68; A61B 2017/8655; A61B 17/7044; A61B 17/7225; A61B 2017/681; A61B 17/17058; A61F 2/0811; A61F 2002/30995
USPC .................. 606/264–279, 287, 288, 289, 290, 606/300–321, 323, 326, 328, 105
See application file for complete search history.

(56) References Cited

U.S. PATENT DOCUMENTS

| | | | | |
|---|---|---|---|---|
| 8,388,660 B1* | 3/2013 | Abdou | ............... | A61B 17/8685 606/267 |
| 2004/0147929 A1* | 7/2004 | Biedermann | ...... | A61B 17/7001 606/266 |
| 2004/0181234 A1* | 9/2004 | McDevitt | ........... | A61B 17/0642 606/104 |
| 2006/0241593 A1* | 10/2006 | Sherman | ............ | A61B 17/7032 606/278 |
| 2007/0073295 A1* | 3/2007 | Biedermann | .......... | A61B 17/68 606/62 |
| 2007/0198018 A1* | 8/2007 | Biedermann | ...... | A61B 17/7032 606/139 |
| 2008/0255619 A1* | 10/2008 | Schneiderman | ... | A61B 17/7007 606/276 |
| 2011/0040339 A1* | 2/2011 | Solomon | ............ | A61B 17/8605 606/312 |
| 2011/0190821 A1* | 8/2011 | Chin | ................... | A61B 17/8685 606/264 |
| 2011/0190830 A1* | 8/2011 | Biedermann | ...... | A61B 17/8685 606/305 |
| 2012/0203286 A1* | 8/2012 | Armstrong | ......... | A61B 17/8685 606/304 |

* cited by examiner

*Primary Examiner* — Pedro Philogene
*Assistant Examiner* — Lynnsy Summitt

(57) ABSTRACT

A bone fastener includes a proximal member having an inner surface that defines an implant cavity and an outer surface including a first threaded portion configured for penetrating fixation with tissue and a second portion. The proximal member defines a longitudinal axis. An intermediate member includes an inner surface extending between a proximal portion connected with the second portion and a distal portion. A distal member includes an outer surface extending between a proximal portion disposed with the distal portion of the intermediate member and a distal portion configured for penetrating fixation with tissue. The distal member is configured for axial translation relative to the intermediate member. Methods of use are disclosed.

18 Claims, 12 Drawing Sheets

BONE FASTENER AND METHODS OF USE

TECHNICAL FIELD

The present disclosure generally relates to medical devices for the treatment of spinal disorders, and more particularly to a spinal implant system including a bone fastener that provides stabilization while reducing stress on spinal elements.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, in accordance with the principles of the present disclosure, a bone fastener is provided. The bone fastener includes a proximal member having an inner surface that defines an implant cavity and an outer surface including a first threaded portion configured for penetrating fixation with tissue and a second portion. The proximal member defines a longitudinal axis. An intermediate member includes an inner surface extending between a proximal portion connected with the second portion and a distal portion. A distal member includes an outer surface extending between a proximal portion disposed with the distal portion of the intermediate member and a distal portion configured for penetrating fixation with tissue. The distal member is configured for axial translation relative to the intermediate member.

In one embodiment, the bone fastener includes a receiver including a pair of spaced apart arms that define an implant cavity configured for disposal of a spinal rod. The receiver further includes an outer surface including a first threaded portion configured for penetrating fixation with a first cortical surface and a second portion. The receiver defines a longitudinal axis. An intermediate member includes an inner surface extending between a proximal portion connected with the second portion and a distal portion. A screw includes an outer surface extending between a proximal portion disposed with the distal portion of the intermediate member and a second threaded portion configured for penetrating fixation with a second cortical surface. One of the receiver and the screw is axially translatable relative to the intermediate member such that the bone fastener is expandable between a first orientation such that one of the first threaded portion and the second threaded portion is engaged with a respective cortical surface and a second orientation such that the other of the threaded portions is engaged with its respective cortical surface.

In one embodiment, in accordance with the principles of the present disclosure, a method for treating a spine is provided. The method includes the steps of: providing a bone fastener comprising a proximal member including an inner surface that defines an implant cavity and an outer surface including a first threaded portion and a second portion, the proximal member defining a longitudinal axis, an intermediate member including an inner surface extending between a proximal portion connected with the second portion and a distal portion, and a distal member including an outer surface extending between a proximal portion disposed with the distal portion of the intermediate member and a distal portion; fastening the first threaded portion with a first cortical surface or the second threaded portion with a second cortical surface to dispose the bone fastener in a first orientation; translating one of the proximal member and the distal member relative to the intermediate member to expand the bone fastener; and fastening the other of the threaded portions with a respective cortical surface to dispose the bone fastener in a second orientation.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
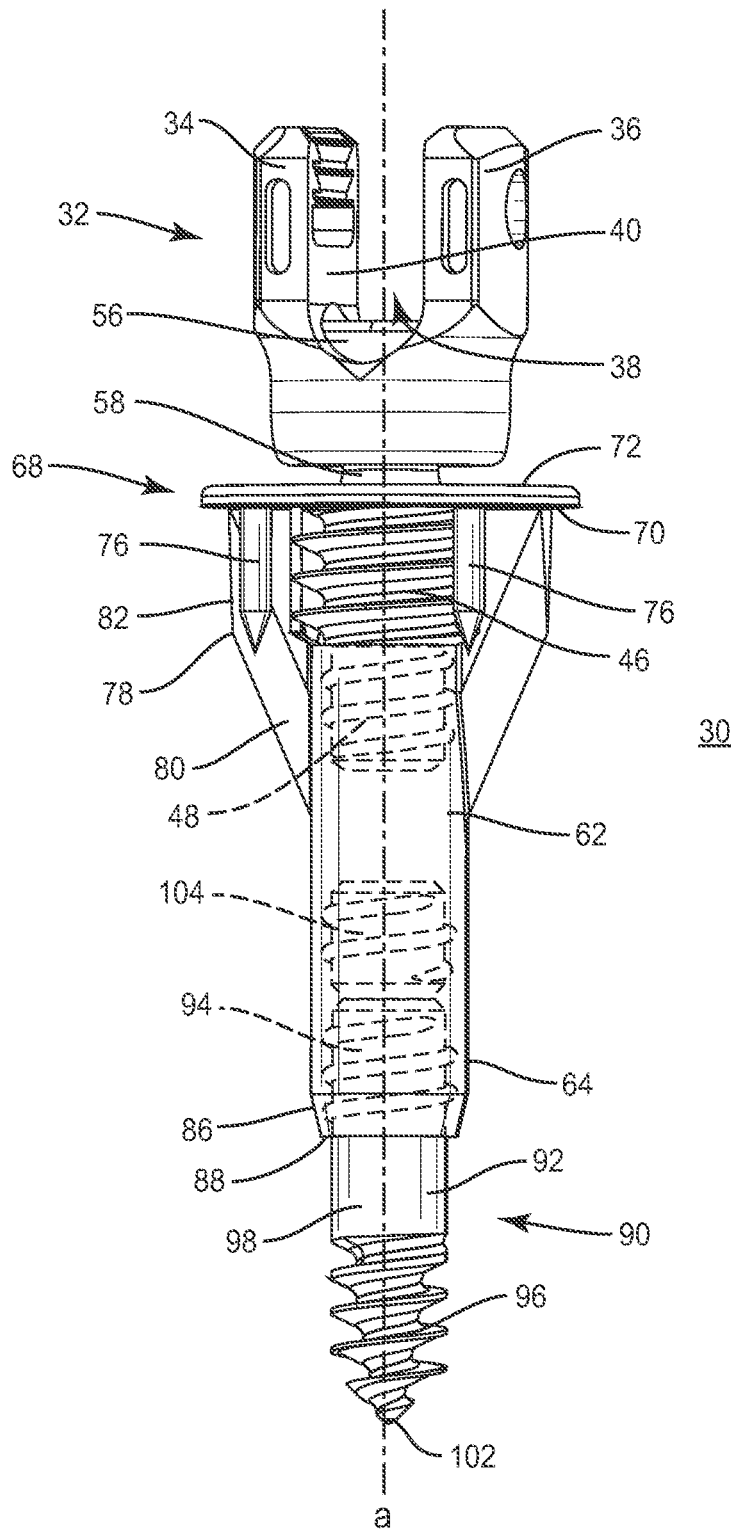
FIG. 1 is a perspective view, in part phantom, of one particular embodiment of a bone fastener of a surgical system in accordance with the principles of the present disclosure.

The exemplary embodiments of a surgical system, a bone fastener and related methods of use disclosed are discussed in terms of medical devices for the treatment of musculoskeletal disorders and more particularly, in terms of a spinal implant system including a bone fastener and a method for treating a spine. In one embodiment, the disclosed surgical system includes a bone fastener configured to achieve bi-cortical fixation with an anatomical trajectory within a sacrum of a patient. It is envisioned that a distal end of bone fastener may telescope or expand either on a threaded shaft or sleeve until bi-cortical fixation is achieved.

In one embodiment, the surgical system includes a bone fastener including a proximal end that is configured to expand until the proximal end is impacted, threaded or stapled into tissue, such as, for example, a first cortical surface. The proximal end of the bone fastener is configured to continue expanding after being impacted, threaded or stapled into the first cortical surface until an opposite cortex is reached. In one embodiment, this configuration may be reversed such that a distal end of the bone fastener is expanded until the distal end is impacted, threaded or stapled into tissue, such as, for example, a cortical surface. The distal end of the bone fastener can continue expanding after being impacted, threaded or stapled into the first cortical surface until the opposite cortical surface is reached.

In one embodiment, the system includes a bone fastener having a threaded proximal end to engage tissue. In one embodiment, the system includes a bone fastener having a proximal end including at least one sharp point to engage tissue. In one embodiment, the system includes a bone fastener configured for use without a plate or sleeve. In one embodiment, the system includes a bone fastener configured for use with a plate or sleeve.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed spinal implant system, including the bone fastener and methods of use may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system including the bone fastener and methods of use of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there is illustrated components of a surgical system including a bone fastener 30 in accordance with the principles of the present disclosure.

The components of the surgical system can be fabricated from biologically acceptable materials suitable for medical applications, including metals, synthetic polymers, ceramics and bone material and/or their composites, depending on the particular application and/or preference of a medical practitioner. For example, the components of the surgical system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the surgical system may have material composites, including the above materials, to achieve various desired characteristics such as strength, rigidity, elasticity, compliance, biomechanical performance, durability and radiolucency or imaging preference. The components of the surgical system, individually or collectively, may also be fabricated from a heterogeneous material such as a combination of two or more of the above-described materials. The components of the surgical system may be monolithically formed, integrally connected or include fastening elements and/or instruments, as described herein.

Fastener 30 includes a proximal member, such as, for example, a receiver 32 defining a longitudinal axis a and including a pair of spaced apart arms 34, 36 that define an implant cavity 38 configured for disposal of a spinal construct, such as, for example, a spinal rod. Arms 34, 36 extend parallel to axis a. It is envisioned that arm 34 and/or arm 36 may be disposed at alternate orientations, relative to axis a, such as, for example, transverse, perpendicular and/or other angular orientations such as acute or obtuse, coaxial and/or may be offset or staggered, according to the requirements of a particular application. Arms 34, 36 each include an arcuate outer surface having at least one recess or cavity configured to receive an insertion tool, compression instrument and/or instruments for inserting and tensioning fastener 30. It is contemplated that the outer surfaces of arms 34, 36 may also be continuous such that the outer surfaces of arms 34, 36 are smooth and/or even.

An inner surface 40 of receiver 32 defines a cavity 38 that is substantially U-shaped. It is envisioned that all or only a portion of cavity 38 may have alternate cross section configurations, such as, for example, V-shaped, W-shaped, oval, oblong triangular, square, polygonal, irregular, uniform, non-uniform, offset, staggered, and/or tapered, depending upon the requirements of a particular application. Surface 40 includes a thread form located adjacent arm 34 and a thread form located adjacent arm 36 each configured for engagement with a coupling member, such as, for example, a setscrew, to retain a spinal construct, such as, for example, a spinal rod within cavity 38. It is envisioned that surface 40 may be disposed with the coupling member in alternate fixation configurations, such as, for example, friction fit, pressure fit, locking protrusion/recess, locking keyway and/or adhesive. It is contemplated that all or only a portion of surface 40 may have alternate surface configurations to enhance engagement with the spinal rod and/or the setscrew such as, for example, rough, arcuate, undulating, mesh, porous, semi-porous, dimpled and/or textured, according to the requirements of a particular application.

Receiver 32 includes a first end 42 having an outer surface 44 defining a first threaded portion 46 configured for penetrating fixation with tissue, such as, for example, a first cortical surface, described below, and a second portion 48 configured to engage an intermediate member 50 to retain receiver 32 with member 50. The thread form configurations on portions 46, 48 are external or male thread forms. It is envisioned that end 42 may include one or a plurality of hooks, anchors, wedges, buttons, clips, snaps, friction fittings, compressive fittings, expanding rivets, staples, nails, adhesives, fixation plates and/or posts. Receiver 32 may be coated with an osteoinductive or osteoconductive material to enhance fixation with tissue and/or engagement with member 50, and/or include one or a plurality of therapeutic agents.

It is contemplated that portion 46 and/or portion 48 may include one thread form configuration or a plurality of different thread form configurations. It is envisioned that the thread form configurations on surface 44 may include a single thread turn or a plurality of discrete threads. In one embodiment, surface 44 includes a portion 52, disposed between portions 46, 48, which is smooth and/or even such that the thread form configurations on surface 44 along portion 46 and portion 48 are non-continuous. It is contemplated that surface 44 may be threaded along portion 52 such that the thread form configurations on surface 44 along portion 46 and portion 48 are continuous.

Portions 46, 48 each have substantially cylindrical cross sectional configurations. Portion 46 has a width w that is greater than a width w1 of portion 48. It is contemplated that surface 44 may include one or a plurality of openings along portion 46 and/or portion 48. It is envisioned that the respective lengths of portions 46, 48 may vary depending upon the requirements of a particular application. It is further envisioned that all or only a portion of end 42 may be variously configured and dimensioned, such as, for example, oval, oblong, square, rectangular, polygonal, irregular, uniform, non-uniform, offset, staggered, tapered, consistent or variable, depending on the requirements of a particular application. End 42 includes an inner surface defining an axial passageway extending through portions 46, 48 along axis a configured for disposal of a tool, such as, for example, a driver.

In one embodiment, end 42 and receiver 32 are monolithically formed and are not movable relative to one another, such as, for example, a mono-axial screw. In one embodiment, receiver 32 includes an aperture 54 extending through surface 40 defining a passageway configured for disposal of end. An upper portion 56 of end 42 has a width that is greater than a width of aperture 54 such that portion 56 is prevented from moving distally through aperture 54 along axis a. Width w of portion 46 is greater than the width of aperture 54 such that portion 46 is prevented from moving proximally through aperture 54 along axis a.

In one embodiment, portion 56 includes an aperture, such as, for example, a tool socket (not shown) defined within and/or recessed in a proximal face of portion 56. The tool socket is configured for disposal of a tool, such as, for example, a driver, capable of rotating portion 56 in a first direction, such as for example, clockwise, and a second direction, such as, for example, counterclockwise, about axis a. It is envisioned that the aperture in portion 56 may have a hexagonal or star-shaped configuration configured for disposal of a correspondingly shaped portion of a driver. In one embodiment, end 42 includes an axial passageway (not shown) extending through portions 56, 46, 48 along axis a configured for movable disposal of a driver, as will be described. It is envisioned that the axial passageway has a width that is less than a width of the aperture in portion 56 such that the longitudinal passageway may extend through the aperture. In one embodiment, portion 56 includes a first tool socket configured to facilitate rotation of the proximal member and the axial passageway has a smaller dimension than the first tool socket such that a driver may pass through the proximal and intermediate members and engage the distal member, as described.

End 42 includes a neck 58 positioned between portion 46 and portion 56 having a width that is less than the width of aperture 54. Neck 58 is configured for disposal within aperture 54 such that receiver 32 is rotatable relative to end 42 through an angular range of 0-360 degrees in a plurality of planes, such as, for example, the sagittal, coronal or transverse plane of a body of a patient for alignment of receiver 32 with a spinal construct, such as, for example, a spinal rod. The spinal rod may be disposed within cavity 38.

Figure 2:
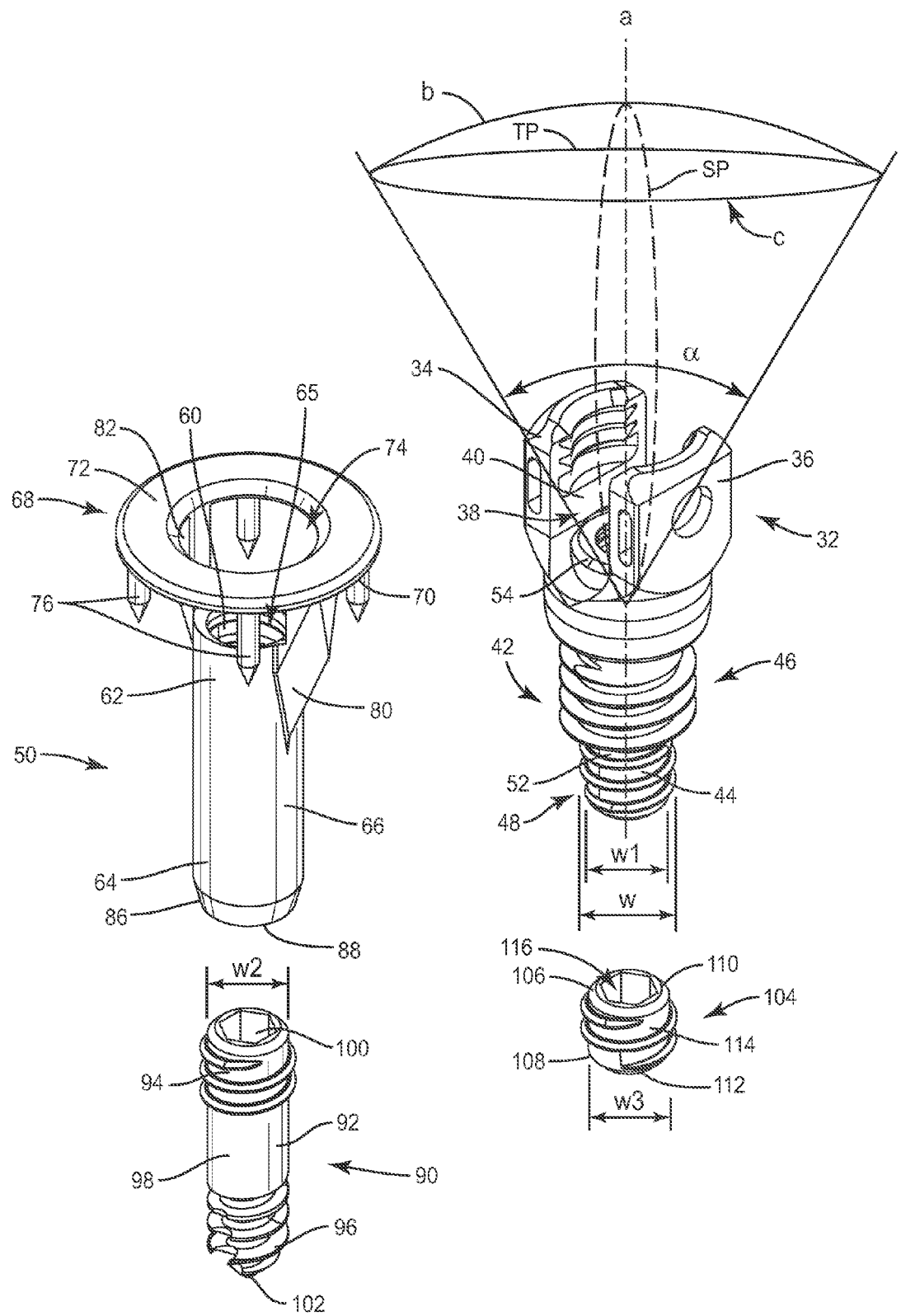
FIG. 2 is a perspective view of the bone fastener shown in FIG. 1 with parts separated.

Receiver 32 is rotatable to a selected angle through and within angular range α relative to axis a in a plurality of planes that lie in a cone configuration C, as shown in FIG. 2. The area and/or volume defined by cone C, which includes the configuration disposed between axis a and a circular base b, is defined by the range of motion of receiver 32 about axis a. The plurality of planes includes a locus of all straight line segments that join axis a and base b. For example, receiver 32 is separately rotatable to a selected angle within angular range a in each plane corresponding to a particular straight line segment that lies in cone configuration C. It is contemplated that receiver 32 may rotatable through the individual diameters, chords, section and/or radii of base b and/or other portions of cone C. In one embodiment, receiver 32 is rotatable to a selected angle within angular range α in a sagittal plane of a body of a patient, corresponding to a particular plane that lies in cone C. In one embodiment, receiver 32 is rotatable to a selected angle within angular range α in a transverse plane of the body, corresponding to a particular plane that lies in cone C. In one embodiment, receiver 32 is rotatable to a selected angle within angular range α in a coronal plane of the body, corresponding to a particular plane that lies in cone C.

Member 50 is configured for disposal within tissue, such as, for example, bone, and includes an inner surface 60 extending between a proximal portion 62 connected with portion 48 and a distal portion 64. Surface 60 defines an axial passageway 65 configured for movable disposal of portion 48 and includes a thread form configuration configured to engage the thread form configuration on surface 44 along portion 48. The thread form configuration in passageway 65 is an internal or female thread form. The width of passageway 65 is constant throughout the length thereof. It is contemplated that the width of passageway 65 may be uniform, non-uniform, staggered, and/or tapered. Passageway 65 has a substantially cylindrical cross sectional configuration. It is envisioned that all or only a portion of passageway 65 may have alternate cross section configurations, such as, for example, oval, oblong triangular, square, polygonal, irregular, uniform, non-uniform, offset, staggered, and/or tapered. In one embodiment, portion 48 is fixed within passageway 65. In one embodiment, end 42 is monolithically formed with member 50.

In one embodiment, the external thread form configuration on surface 44 along portion 48 has a major diameter that is greater than the width of passageway 65 and a minor diameter that is less than or equal to a width of passageway 65 such that the thread form configuration on surface 44 along portion 48 is disposed within the internal thread form configuration in passageway 65 such that surface 44 engages surface 60 when end 42 is disposed within passageway 65 to prevent lateral movement of end 42 within passageway 65.

The thread form configuration on surface 44 engages the thread form configuration on surface 60 to facilitate axial translation of receiver 32 relative to member 50. In one embodiment, a driver is engageable with the tool socket of portion 56 such that end 42 can be rotated a first direction, such as, for example, a clockwise direction as shown by arrow A in FIG. 4 and a second direction, such as, for example, a counter clockwise direction as shown by arrow AA relative to member 50 within passageway 65 such that end 42 telescopes within passageway 65 to facilitate axial translation of receiver 32 relative to member 50. For example, rotating portion 56 in the direction shown by arrow A causes end 42 to axially translate along passageway 65 in the direction shown by arrow B. For example, rotating portion 56 in the direction shown by arrow AA causes end 42 to axially translate along passageway 65 in a direction shown by arrow BB.

Member 50 includes an arcuate outer surface 66 that is smooth and/or even to prevent fastener member 50 from toggling during implantation of member 50 within tissue, for example. It is contemplated that all or only a portion of surface 66 may have various surface configurations, such as, for example, rough, threaded, arcuate, undulating, porous, semi-porous, dimpled, polished and/or textured, to enhance fixation of member 50 with tissue.

Portion 62 includes a plate 68 having a first planar surface 70 configured to engage tissue and a second planar surface 72 configured to engage receiver 32, as will be discussed. Plate 68 is substantially circular. In one embodiment, surface 70 includes at least one bone penetrating element extending therefrom, such as, for example, a spike 76. Surface 70 includes a plurality of spikes 76 extending therefrom and disposed radially about surface 70 in a circumferential orientation. It is contemplated that other engaging structures and/or bone penetrating elements may be located on surface 70, such as, for example, nails, barbs, expanding elements and/or protrusions to facilitate engagement of plate 68 with tissue, such as, for example, bone. It is further contemplated that the engaging structures and/or bone penetrating elements on surface 70 may be variously configured, such as, for example, uniform, non-uniform, or staggered, depending on the requirements of a particular application. It is envisioned that all or only a portion of plate 68 may be variously configured and dimensioned, such as, for example, circular, oval, oblong, triangular, square, rectangular, polygonal, or irregular, depending on the requirements of a particular application.

Plate 68 has a height between surfaces 70, 72, which is substantially uniform such that plate 68 has a disc shaped configuration. It is contemplated that the height of plate 68 between surfaces 70, 72 may vary such that the height of one side of plate 68 is different than the height of another side of plate 68 such that plate has a wedge shaped configuration. In one embodiment, plate 68 is disposed at an acute angular orientation relative to axis a to maximize surface contact with tissue such as, for example, bone. It is envisioned that plate 68 may be disposed through angular ranges in various orientations relative to axis a, such as, for example, transverse, perpendicular and/or other angular orientations such as acute or obtuse, and/or may be offset or staggered.

Plate 68 defines an opening 74 extending through surfaces 70, 72 configured for insertion and removal of end 42 and/or a distal member, such as, for example, a screw 90. Opening 74 is in communication with passageway 65. Opening 74 is substantially circular and has a width that is greater than width w of portion 46 such that portions 46, 48 may be advanced distally along axis a through opening 74. The thread form configuration on surface 44 along portion 46 has a major diameter that is greater than a width of opening 74 and a minor diameter that is less than or equal to the width of opening 74 such that portion 46 may movably engage opening 74 to advance end 42 distally along axis a within opening 74 until the thread form configuration on surface 44 along portion 46 is positioned below surface 70 to prevent end 42 from moving proximally along axis a through opening 74. It is envisioned that opening may have alternate cross section configurations, such as, for example, oval, oblong triangular, square, polygonal, irregular, uniform, non-uniform, offset, staggered, and/or tapered.

In one embodiment, surface 66 includes at least one connecting element extending therefrom, such as, for example, an arm 78 to connect plate 68 with member 50. Surface 66 includes a plurality of arms 78 extending therefrom and disposed radially about surface 66 in a circumferential orientation. Arms 78 include a first part 80 extending from surface 66 such that first part 80 is disposed at an acute angle relative to longitudinal axis a and a second part 82 extending between part 80 and surface 70 such that part 82 is parallel to axis a. In one embodiment, fastener 30 includes a pair of arms 78 disposed opposite one another such that each arm is positioned an equal distance from two adjacent spikes 76. It is envisioned that part 80 and/or part 82 may be disposed at alternate orientations relative to longitudinal axis a, such as, for example, parallel, transverse, perpendicular and/or other angular orientations such as acute or obtuse and/or may be offset or staggered, depending on the requirements of a particular application. It is further envisioned that the relative positioning of arms 78 may be variously configured, such as, for example, uniform, non-uniform, or staggered, depending on the requirements of a particular application.

Member 50 includes a tapered portion 86 extending between portion 64 and a distal face 88 configured to facilitate disposal of member 50 within tissue, such as, for example, bone. It is envisioned that portion 86 may extend from portion 62 to face 88 such that portion 86 extends substantially the entire length of surface 66. It is envisioned that member 50 may be variously configured and dimensioned between portion 62 and face 88 and/or portion 64 and face 88, such as, for example, planar, concave, convex, polygonal, irregular, uniform, non-uniform, staggered, tapered, consistent or variable, depending on the requirements of a particular application.

Screw 90 includes an outer surface 92 extending between a proximal portion 94 disposed with portion 64 and a second threaded portion 96 configured for penetrating fixation with tissue, such as, for example, a second cortical surface, as will be described. Surface 92 includes an external thread form configuration along portion 94. It is contemplated that portion 94 and/or portion 96 may include one thread form configuration or a plurality of different thread form configurations. It is envisioned that the thread form configurations on surface 92 along portion 94 and/or portion 96 may include a single thread turn or a plurality of discrete threads. Screw 90 includes an unthreaded portion 98 between portions 94, 96 such that the thread form configurations on surface 92 along portion 94 and portion 96 are non-continuous. It is contemplated that portion 98 may be threaded such that the thread form configurations on surface 92 along portion 94 and portion 96 are continuous. It is further contemplated that other engaging structures may be located along surface 92 along portion 94 and/or portion 96, in place of or in addition to the thread form configurations discussed above, such as, for example, a nail configuration, barbs, expanding elements, raised elements and/or spikes to facilitate engagement of portion 96 with tissue, such as, for example, cortical bone and/or portion 94 with member 50.

The threads on surface 92 along portion 94 engage the threads on surface 60 within passageway 65 to facilitate axial translation of screw 90 relative to member 50. In one embodiment, a driver is engageable with a tool socket of screw 90, described below, such that the threads on surface 92 along portion 94 are aligned with the threads on surface 60 within passageway 65 such that screw 90 may be rotated a first direction, such as, for example, a clockwise direction as shown by arrow C in FIG. 3 and a second direction, such as, for example, a clockwise direction as shown by arrow CC, relative to member 50 within passageway 65 such that screw 90 telescopes within passageway 65 to facilitate axial translation of screw 90 relative to member 50. For example, rotating screw 90 in the direction shown by arrow C causes screw 90 to axially translate along passageway 65 in a direction shown by arrow D. For example, rotating screw 90 in the direction shown by arrow CC causes screw 90 to axially translate along passageway 65 in a direction shown by arrow DD.

Portion 94 has a width w2 that is equivalent to width w1 of portion 48. Screw 90 includes a pointed tip 102 at a distal end of portion 96 that has a width that is less than width w2 of portion 94 such that screw 90 is tapered between portion 94 and tip 102. It is envisioned that all or only a portion of screw 90 may be variously configured and dimensioned, such as, for example, polygonal, irregular, uniform, non-uniform, staggered, tapered, consistent or variable, depending on the requirements of a particular application.

In one embodiment, the external thread form configuration on surface 92 along portion 94 has a major diameter that is greater than the width of passageway 65 and a minor diameter that is less than or equal to the width of passageway 65 such that the thread form configuration on surface 92 along portion 94 is disposed within the internal thread form configuration in passageway 65 such that surface 92 engages surface 60 when portion 94 is disposed within passageway 65 to prevent lateral movement of screw 90 within passageway 65. When end 42 and portion 94 are disposed in passageway 65, receiver 32 and screw 90 are disposed in a coaxial orientation.

Screw 90 includes an inner surface defining a tool socket 100 extending through portion 94 along axis a that is in communication with both the axial passageway extending through end 42 and passageway 65 such that a tool, such as, for example, a driver and/or an insertion instrument may be advanced through receiver 32 and member 50 and into socket 100 to facilitate penetrating fixation of screw 90 with tissue.

Figure 5:
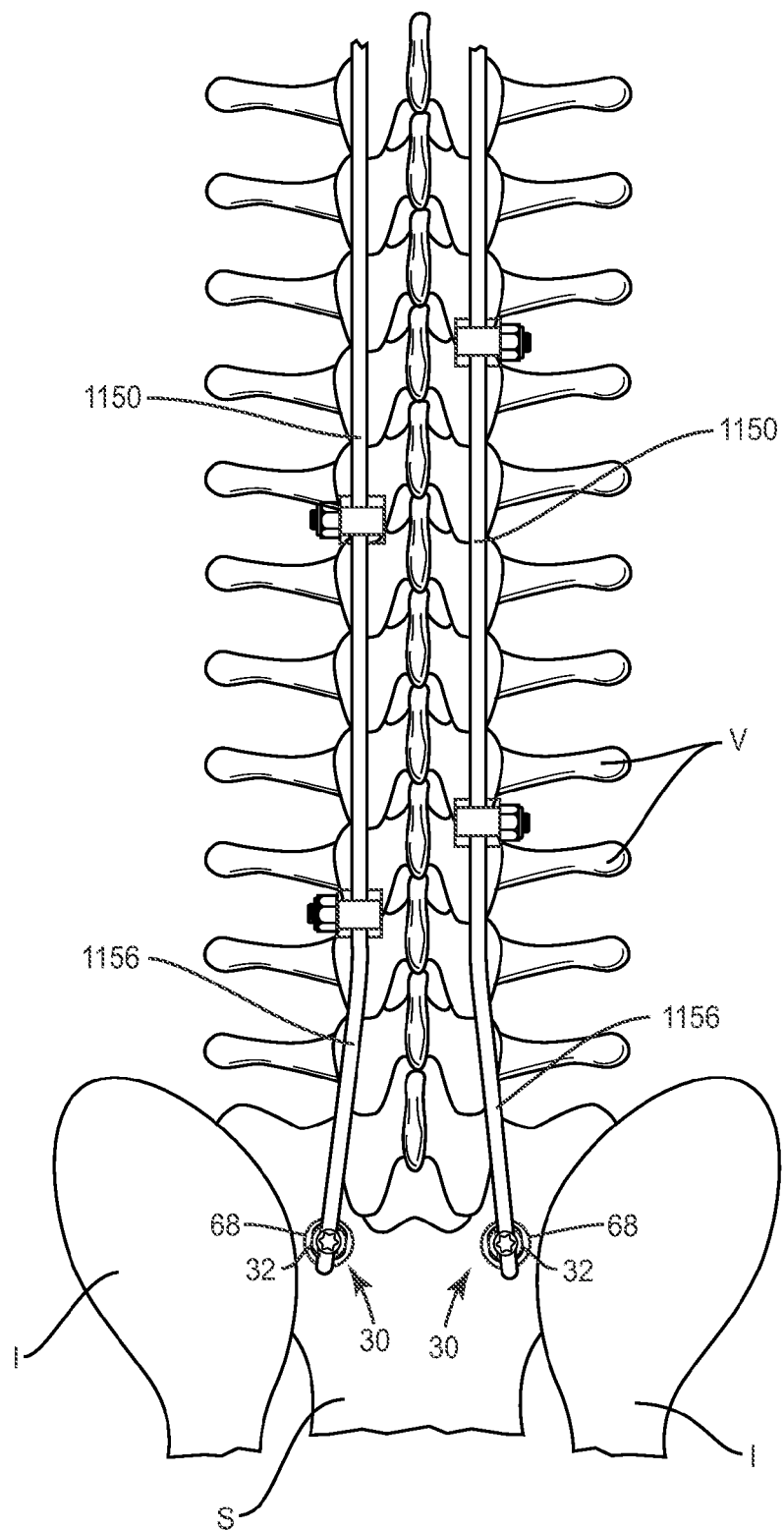
FIG. 5 is a plan view of one embodiment of a surgical system in accordance with the principles of the present disclosure disposed with vertebrae.
Figure 6:
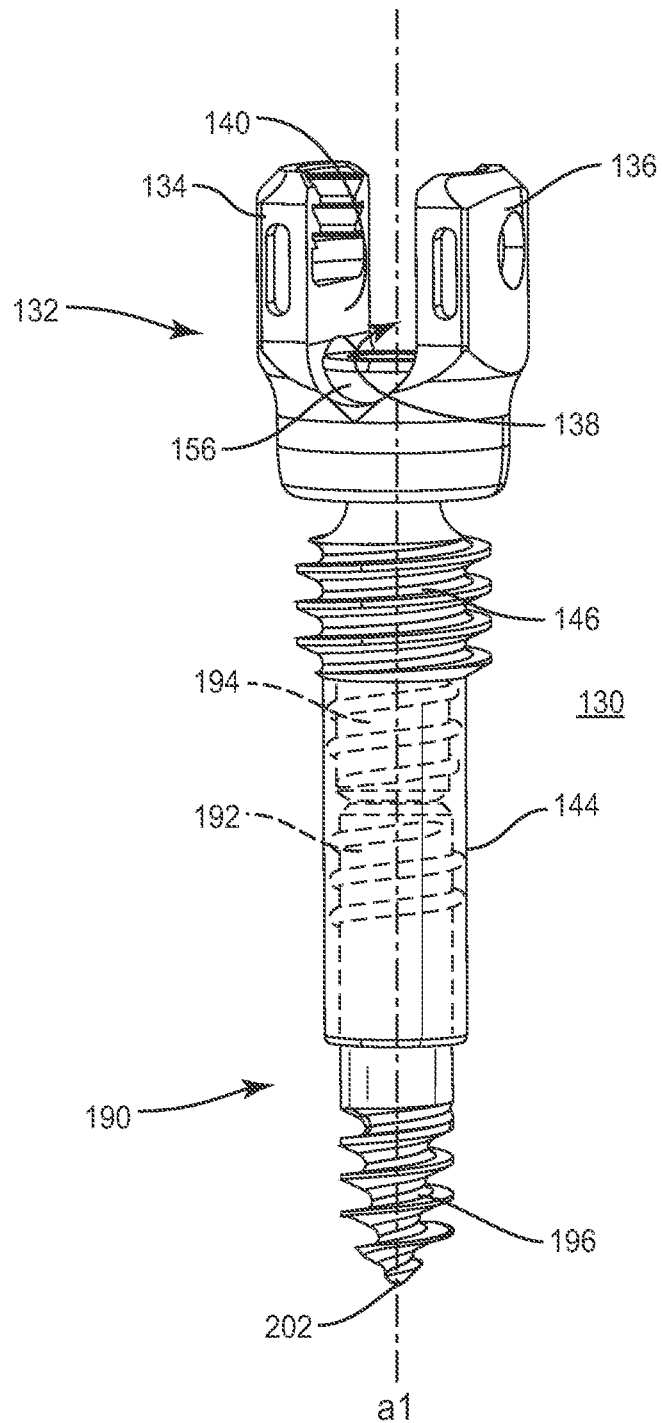
FIG. 6 is a perspective view, in part phantom, of one embodiment of a bone fastener of a surgical system in accordance with the principles of the present disclosure.
Figure 7:
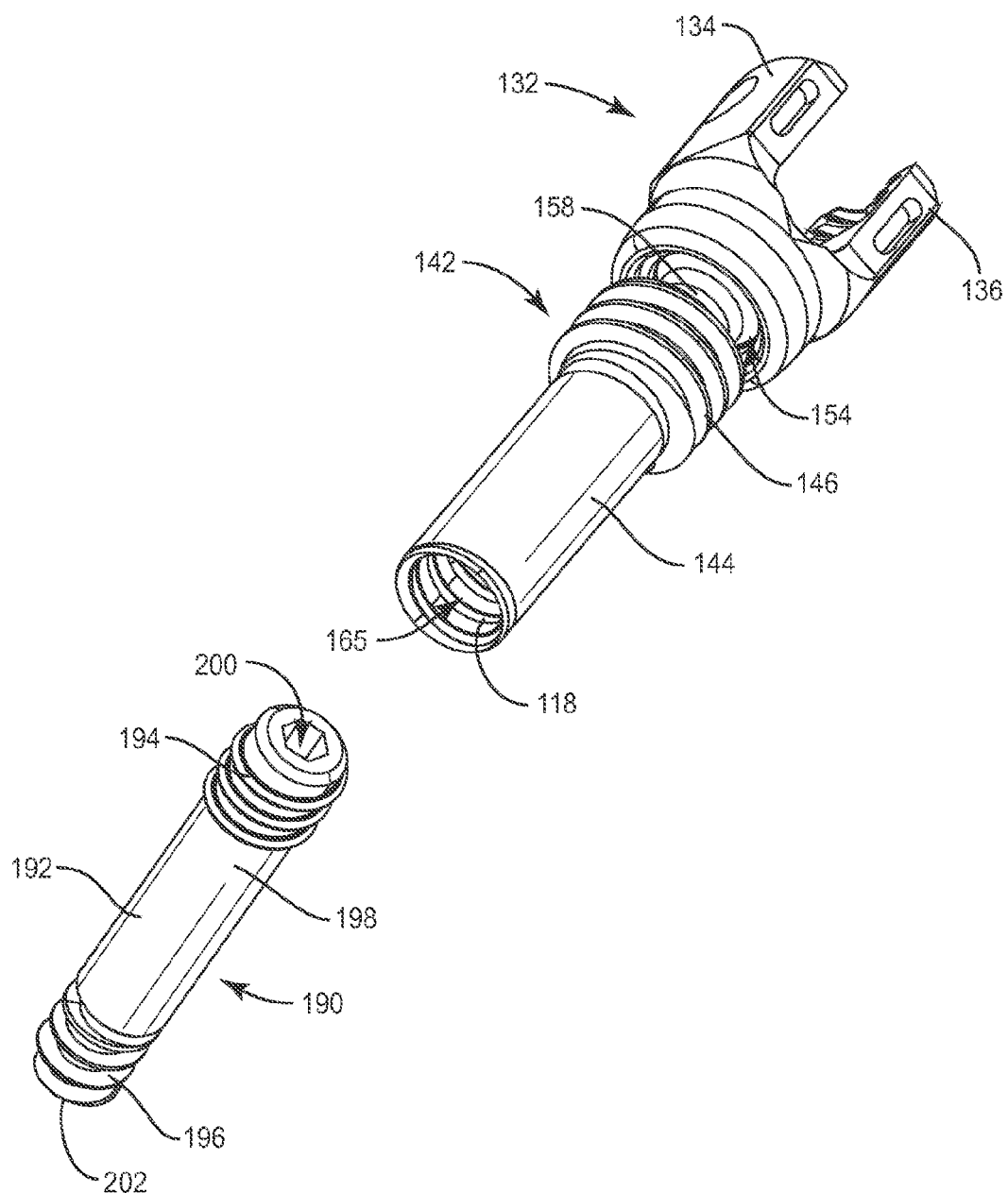
FIG. 7 is a perspective view of the bone fastener shown in FIG. 6 with parts separated.

In assembly, operation and use, a surgical system including bone fastener 30, similar to that described, is employed with a surgical procedure for treatment of a spinal disorder affecting a section of a spine of a patient, as discussed herein. In particular, the surgical system, including fastener 30, is employed with a surgical procedure for treatment of a condition or injury of an affected section of the spine including vertebrae V, as shown in FIG. 5. In one embodiment, the system including fastener 30 is attached to a sacrum S for a surgical arthrodesis procedure, such as a fusion of the affected section of the spine to facilitate healing and therapeutic treatment. In one embodiment, the system including fastener 30 is attached to vertebrae V, sacrum S and/or ilium I for a dynamic stabilization application.

In use, to treat the affected section of the spine, a medical practitioner obtains access to a surgical site including sacrum S and vertebrae V in any appropriate manner, such as through incision and retraction of tissues. It is envisioned that the components of the surgical system may be used in any existing surgical method or technique including open surgery, mini-open surgery, minimally invasive surgery including percutaneous surgical implantation, whereby sacrum S and vertebrae V are each accessed through a micro-incision, or sleeve that provides a protected passageway to the area. Once access to the surgical site(s) are obtained, the particular surgical procedure is performed for treating the spinal disorder. The components of the surgical system, including fastener 30 are employed to augment the surgical treatment. Fastener 30 and a spinal implant, such as, for example, a vertebral rod 1150 can be delivered or implanted as a pre-assembled device or can be assembled in situ. The surgical system may be may be completely or partially revised, removed or replaced.

Figure 3:
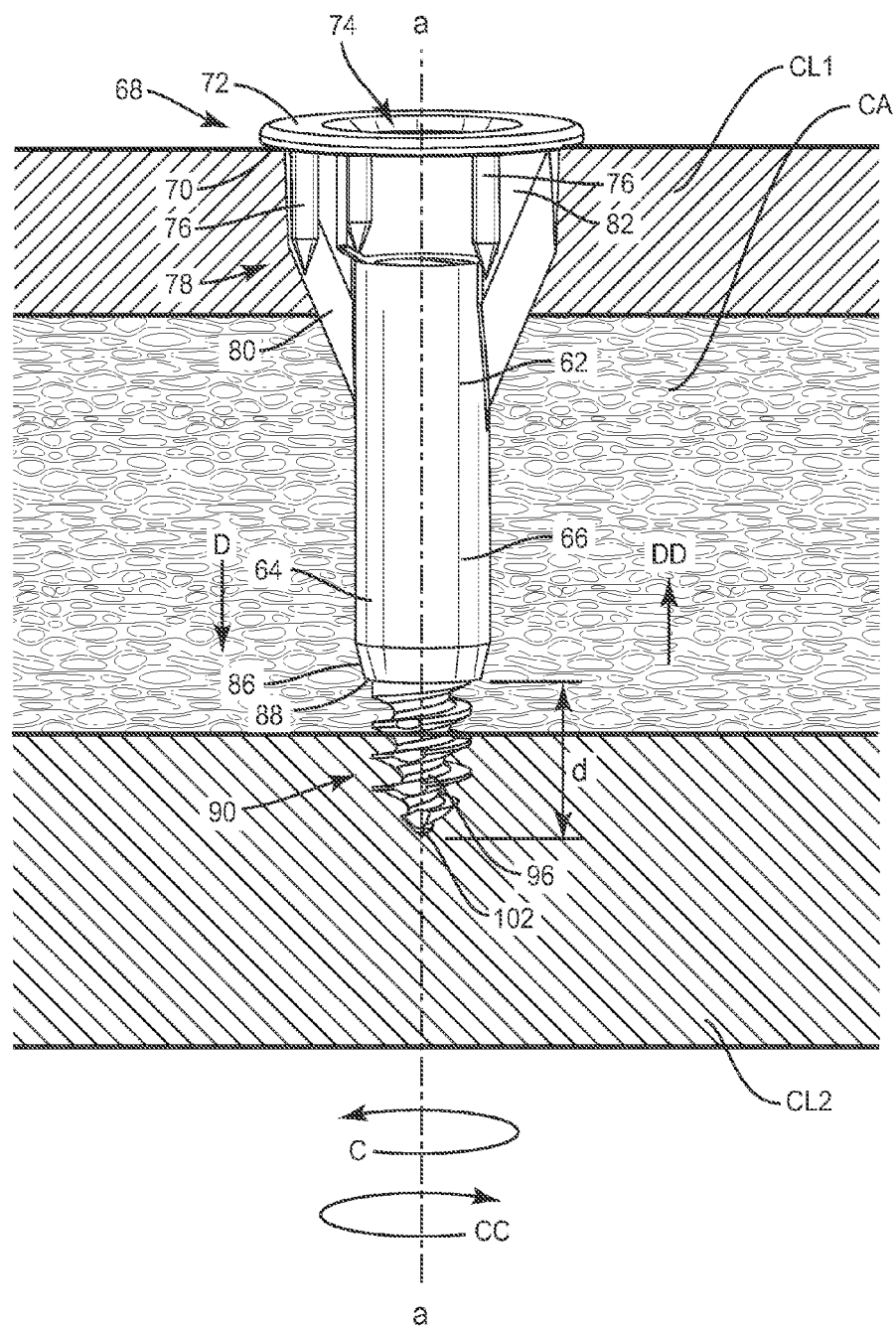
FIG. 3 is a perspective view of a component of the bone fastener shown in FIG. 1 disposed with tissue.
Figure 4:
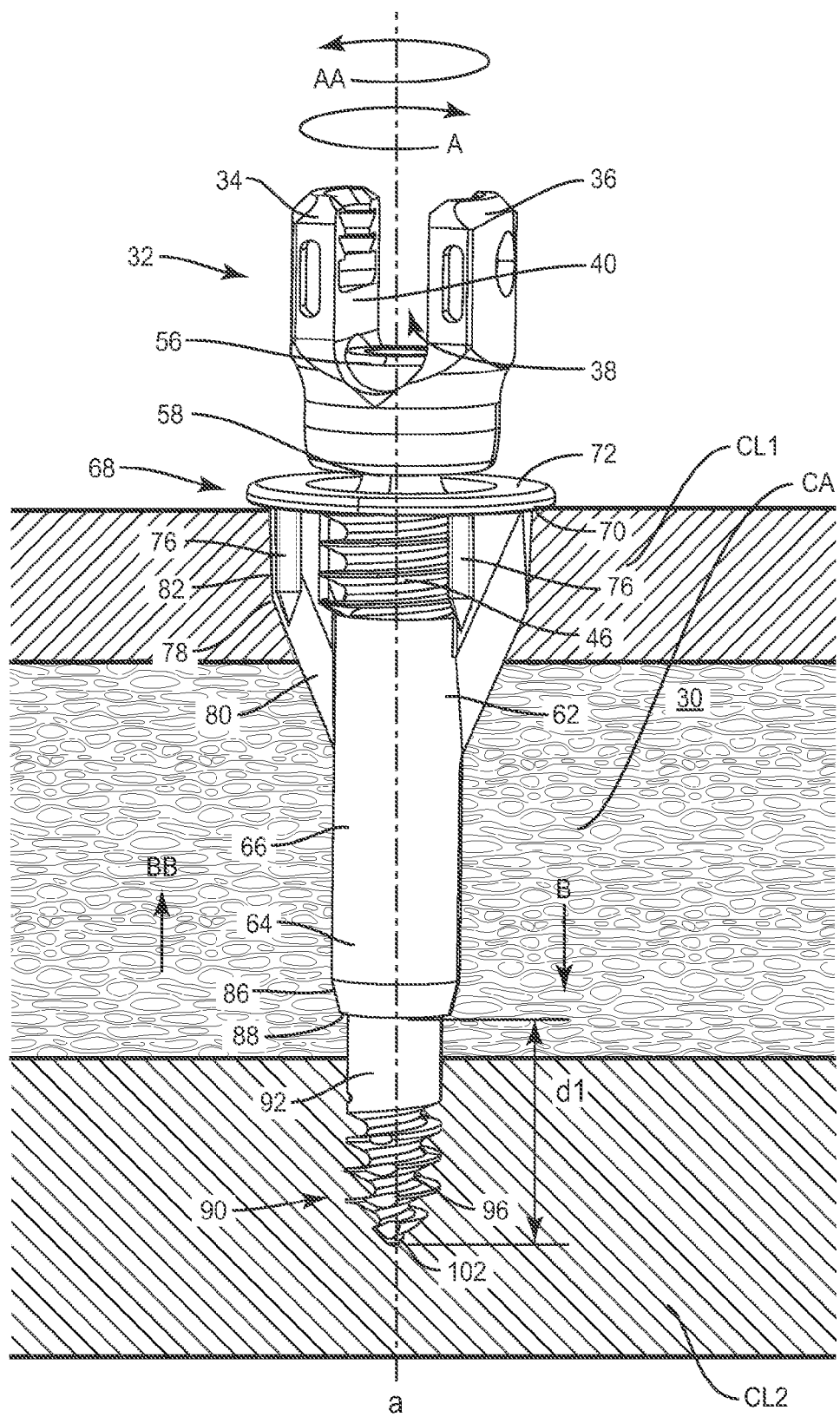
FIG. 4 is a perspective view of the bone fastener shown in FIG. 1 disposed with tissue.

The surgical system includes two axially aligned and spaced apart rods 1150 that extend to adjacent a sacroiliac region (SIR) of the patient. Rods 1150 each have a rigid, arcuate portion 1156 extending across sacrum S of region SIR. A first fastener 30 and a second fastener 30 are configured for fixation with spaced apart regions of sacrum S. The spaced apart regions of sacrum S are each composed of a layer of cancellous bone CA disposed between a first cortical layer, such as, for example, a superior cortical plate CL1 and a second cortical layer, such as, for example, an inferior cortical plate CL2, as shown in FIGS. 3 and 4. Cortical plates CL1, CL2 include bone that is denser and/or less porous than cancellous bone CA. In one embodiment, the system may be utilized in connection with other tissue of a patient's anatomy that include a layer of cancellous bone between layers of cortical bone, such as, for example, ilium I and/or one or more vertebrae.

Receiver 32 and screw 90 are axially translatable relative to member 50 such that each fastener 30 is expandable between a first orientation such that one of portion 46 and portion 96 is engaged with a respective cortical layer of sacrum S and a second orientation such that the other of portion 46 and portion 96 is engaged with the other respective cortical layer.

Pilot holes are made in the regions of sacrum S corresponding to each fastener 30 for receiving members 50. Portions 64 are inserted or otherwise connected to the regions of sacrum S such that portions 64 pass through cortical plate CL1 and penetrate into cancellous bone CA, according to the particular requirements of the surgical treatment. For each fastener 30, member 50 is advanced distally along axis a into sacrum S until surface 70 engages cortical plate CL1, as shown in FIG. 3. Spikes 76 are driven for fixation and penetration with cortical plate CL1.

Screw 90 is inserted through opening 74 and into passageway 65 such that surface 92 along portion 94 is aligned with surface 60 along passageway 65. Tip 102 extends beyond face 88 within cancellous bone CA a distance d from face 88, as shown in FIG. 3. A driver is passed through opening 74, passageway 65 and engaged with tool socket 100. The driver rotates screw 90 in a clockwise direction, as shown by arrow C in FIG. 3 such that the external thread form configuration on surface 92 engage the internal thread form configuration on surface 60. Screw 90 axially translates within passageway 65, in the direction shown by arrow D.

As screw 90 is rotated and axially translates, the distance increases between tip 102 and face 88. Screw 90 advances, in the direction shown by arrow D, along axis a such that tip 102 advances for penetration and fixation with cortical plate CL2 such that tip 102 is disposed a distance d1 from face 88, as shown in FIG. 4, and fastener 30 is disposed in the first orientation. Surface 92 is disposed with cortical plate CL2.

End 42 is inserted through opening 74 and into passageway 65 such that the external thread form configuration on surface 44 along portion 48 are aligned with the internal thread form configuration on surface 60 along passageway 65. A driver is engaged with the tool socket of portion 56 to rotate end 42 in a clockwise direction, as shown by arrow A in FIG. 4, such that the external thread form configuration on surface 44 along portion 48 engages the internal thread form configuration on surface 60 along passageway 65.

End 42 is rotated such that the thread form configuration on surface 44 axially translates beyond surface 70. Surface 44 engages cortical plate CL1 to penetrate and fix portion 46 with cortical plate CL1 such that fastener 30 is disposed in the second orientation. In one embodiment, end 42 may be rotated in the direction shown by arrow A and/or the direction shown by arrow AA to adjust the amount of axial translation of end 42 relative to member 50. This adjustment of end 42 facilitates adjustment of receiver 32 relative to cortical plate CL1 to accommodate the orientation and position of portion 1156 including, for example, the spaced apart distance of portion 1156 relative to cortical plate CL1.

Receiver 32 is selectively and freely rotatable relative to end 42 such that portion 1156 may be aligned for disposal within cavities 38. According to the orientation and position of each rod 1150, fasteners 30 are independently and selectively positioned such that each cavity 38 is selectively rotatable relative to end 42. Each cavity 38 is relatively rotatable to receive, engage and accommodate the orientation and position of portions 1156. This configuration allows orientation of each cavity 38 to receive each of portions 1156 such that receivers 32 can capture rods 1150.

Coupling elements, such as, for example, setscrews may be torqued and threaded with each receiver 32 to securely attach rods 1150 with the respective regions of sacrum S. Each setscrew may be threaded into a threaded portion of surface 40 along arms 36, 38 such that the setscrew engages rod 1150. As the setscrew is threaded into arms 36, 38, the setscrew applies a force to rod 1150 disposed with cavity 38. This force is transmitted through rod 1150 such that rod 1150 engages the surfaces that define cavity 38 causing at least a portion of receiver 32 to engage surface 72. This configuration fixes fastener 30 in an orientation to prevent receiver 32 from moving relative to end 42 such that fastener 30 may receive and accommodate the orientation and position of rods 1150. In one embodiment, upon completion of the procedure, the surgical instruments and non-implant components of the surgical system are removed from the surgical site and the incision is closed.

In one embodiment, as shown in FIGS. 1 and 2, fastener 30 includes a spacer 104 extending between a first end 106 and a second end 108. Spacer 104 has a maximum width w3 that is equivalent to width w1 of portion 48 and width w2 of portion 94. Spacer 104 is tapered between end 106 and a first face 110 and between end 108 and a second face 112 such that faces 110, 112 each have a width that is less than width w3. Spacer 104 includes an outer surface 114 including a thread form configuration that is similar to the thread form configuration on surface 44 along portion 48 and the thread form configuration on surface 92 along portion 94. The thread form configuration on surface 114 is an external or male thread form. The external thread form configuration on surface 114 has a major diameter that is greater than the width of passageway 65 and a minor diameter that is less than or equal to the width of passageway 65 such that the thread form configuration on surface 114 is disposed within the internal thread form configuration in passageway 65 such that surface 114 engages surface 60 when spacer 104 is disposed within passageway 65 to prevent lateral movement of spacer 104 within passageway 65. It is contemplated that other engaging structures may be located along surface 114, in place of or in addition to the thread form configuration discussed above, such as, for example, a nail configuration, barbs and/or expanding elements to facilitate engagement of spacer 104 with member 50. Spacer 104 includes an inner surface defining a passageway 116 extending the length of spacer 104 and through ends 106, 108. Passageway 116 is in communication with the axial passageway in end 42, passageway 65, opening 74 and socket 100, such that an instrument, for example may pass through the axial passageway in end 42, passageway 65, opening 74 and passageway 116 and into socket 100.

Spacer 104 is configured for disposal within passageway 65 to separate end 42 and portion 94 when receiver 32 and screw 90 are disposed in passageway 65. It is envisioned that spacer 104 may prevent axial translation of end 42 or screw 90 in at least one direction when receiver 32 and screw 90 are disposed in passageway 65. It is contemplated that face 112 may engage portion 94 to prevent screw 90 from translating proximally within passageway 65 along axis a. It is further contemplated that face 110 may engage portion 48 to prevent end 42 from translating distally within passageway 65 along axis a.

Portion 48, portion 94 and spacer 104 each have a length that is approximately equivalent to one another. A combined length of portion 48, portion 94 and spacer 104 is less than a length of passageway 65 such that portion 48, portion 94 and spacer 104 may all fit within passageway 65 simultaneously. It is contemplated that the respective lengths of portion 48, portion 94 and spacer 104 may vary such that at least one of portion 48, portion 94 and spacer 104 has a length that is different from at least one of portion 48, portion 94 and spacer 104. It is further contemplated that the combined length of portion 48, portion 94 and spacer 104 may be greater than the length of passageway.

In one embodiment, as shown in FIGS. 6-9, the surgical system includes a fastener 130, similar to fastener 30 and methods described with regard to FIGS. 1-5. Fastener 130 includes a receiver 132 defining a longitudinal axis a1 and including a pair of spaced apart arms 134, 136 that define an implant cavity 138 configured for disposal of a spinal rod. Arms 134, 136 extend parallel to axis a. Arms 134, 136 each include an arcuate outer surface having at least one recess or cavity configured to receive an insertion tool, compression instrument and/or instruments for inserting and tensioning fastener 130. An inner surface 140 of receiver 132 defines cavity 138 and is concavely curved such that cavity 138 is substantially U-shaped. Surface 140 includes a thread form located adjacent arm 134 and a thread form located adjacent arm 136 each configured for engagement with a setscrew to retain a spinal rod within cavity 138.

Receiver 132 includes a first end 142 having an outer surface 144 defining a threaded portion 146 configured for penetrating fixation with tissue, such as, for example, a first cortical surface, described below. In one embodiment, end 142 and receiver 132 are monolithically formed and are not movable relative to one another. In one embodiment, receiver 132 includes an aperture 154 extending through surface 140 defining a passageway configured for disposal of end 142 to movably engage end 142 with receiver 132. An upper portion 156 of end 142 has a width that is greater than a width of aperture 154 such that portion 156 is prevented from moving distally through aperture 154 along axis a1. The maximum width of end 142 is greater than the width of aperture 154 such that end 142 is prevented from moving proximally through aperture 154 along axis a1.

In one embodiment, portion 156 includes an aperture, such as, for example, a tool socket (not shown) defined within and/or recessed in a proximal face of portion 156. The tool socket is configured for disposal of a tool, such as, for example, a driver, capable of rotating portion 156 in a first direction, such as, for example, clockwise, and a second direction, such as, for example, counterclockwise, about axis a1. In one embodiment, end 142 includes an axial passageway (not shown) extending through portions 156, 146 along axis a1 configured for movable disposal of a driver, as will be described. It is envisioned that the axial passageway has a width that is less than a width of the aperture in portion 156 such that the longitudinal passageway may extend through the aperture. In one embodiment, portion 156 includes a first tool socket configured to facilitate rotation of the proximal member and the axial passageway has a smaller dimension than the first tool socket such that a driver may pass though receiver 132 and engage screw 190, as described.

A distal portion of end 142 includes a distal face 188. End 142 includes a neck 158 positioned between end 142 and portion 156 having a width that is less than the width of aperture 154. Neck 158 is concavely curved in a circumferential orientation and is configured for disposal within aperture 154 such that receiver 132 is rotatable relative to end 142 through an angular range of 0-360 degrees in a plurality of planes, such as, for example, the sagittal, coronal or transverse plane of a body of a patient for alignment of receiver 132 with of a spinal rod such that the spinal rod may be disposed within cavity 138. Receiver 132 is rotatable to a selected angle through and within angular range relative to axis a1 in a plurality of planes that lie in a cone configuration, similar to that shown with regard to fastener 30 in FIG. 2.

Receiver 132 includes an inner surface 118 defining a passageway 165 having an internal or female thread form configuration configured to engage an external or male thread form on an outer surface 192 of a screw 190 to retain receiver 132 with screw 190.

Screw 190 extends between a proximal portion 194 configured for disposal within passageway 165 and a second threaded portion 196 configured for penetrating fixation with a second cortical surface, such as for example, an inferior cortical plate of a sacrum. Screw 190 includes an unthreaded portion 198 between portions 194, 196 such that the thread form configurations on surface 192 along portion 194 and portion 196 are non-continuous. In one embodiment, the external thread form configuration on surface 192 has a major diameter that is greater than the width of passageway 165 and a minor diameter that is less than or equal to the width of passageway 165 such that the thread form configuration on surface 192 along portion 194 is disposed within the internal thread form configuration in passageway 165 such that surface 192 engages surface 118 when portion 194 is disposed within passageway 165 to prevent lateral movement of screw 190 within passageway 165.

Screw 190 includes an inner surface defining a tool socket 200 extending into portion 194 along axis a1 that is in communication with the axial passageway extending through portion 156 and passageway 165 such that a tool, such as, for example, a driver may be advanced through receiver 132 and into socket 200 to facilitate penetrating fixation of screw 190 with tissue. Socket 200 is hexagonal and is configured for disposal of a correspondingly shaped portion of an instrument therein. Screw 190 includes a pointed tip 202 at a distal end of portion 196 that has a width that is less than a width of portion 194 such that screw 190 is tapered between portion 194 and tip 202.

The thread form configuration on surface 192 along portion 194 engages the thread form configuration on surface 118 to facilitate axial translation of screw 190 relative to end 142. Screw 190 may be rotated a first direction, such as, for example, a clockwise direction as shown by arrow E in FIG. 9 and a second direction, such as, for example, a counterclockwise direction as shown by arrow EE relative to end 142 within passageway 165 such that screw 190 telescopes within passageway 165 to facilitate axial translation of screw 190 relative to end 142. For example, rotating screw 190 in the direction shown by arrow E causes screw 190 to axially translate along passageway 165 in the direction shown by arrow F. For example, rotating screw 190 in a direction shown by arrow EE causes screw 190 to axially translate along passageway 165 in a direction shown by arrow FF.

In one embodiment, the surgical system including fastener 130 is attached to sacrum S for a surgical arthrodesis procedure, such as a fusion of the affected section of the spine, such as, for example, the sacroiliac joint, to facilitate healing and therapeutic treatment. In one embodiment, the system including fastener 130 is attached to vertebrae V, sacrum S and/or ilium I for a dynamic stabilization application.

Receivers 132 and screws 190 are axially translatable relative to one another such that each fastener 130 is expandable between a first orientation such that one of portion 146 and portion 196 is engaged with a respective cortical layer of sacrum S (FIG. 5), such as for example, plate CL1 or plate CL2 and a second orientation such that the other of portion 146 and portion 196 is engaged with the other cortical layer.

Figure 8:
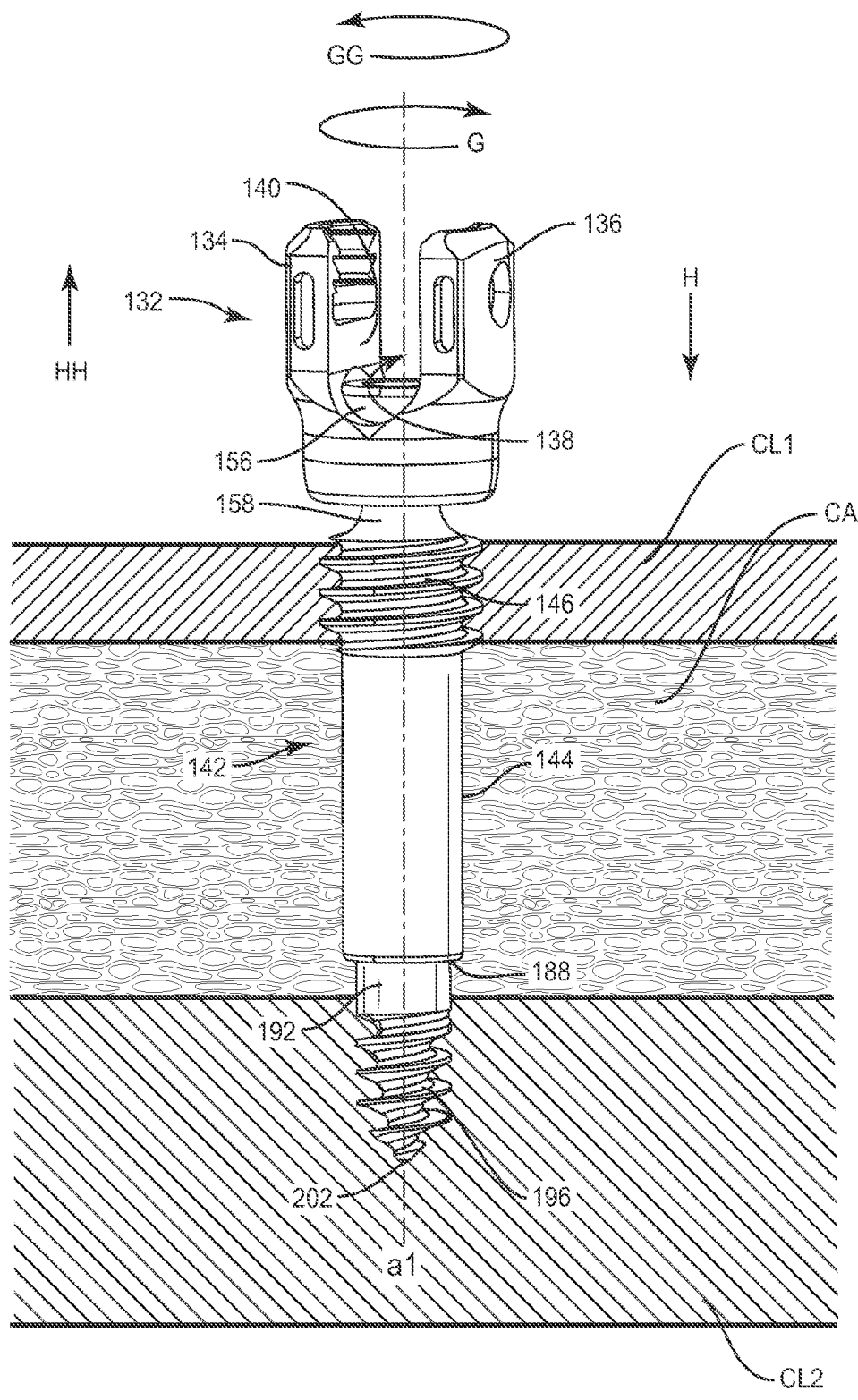
FIG. 8 is a perspective view of the bone fastener shown in FIG. 6 disposed with tissue.

Pilot holes are made in sacrum S for receiving each of fasteners 130. Receiver 132, with screw 190 engaged therewith, of each fastener 130 is inserted into the respective pilot holes. A driver is engaged with the tool socket of portion 156 to rotate portion 156, in the direction shown by arrow G, such that fasteners 130 axially translate within sacrum S, in the direction shown by arrow H. Portion 156 is rotated, in the direction show by arrow G, until tip 202 passes through cortical plate CL1 and penetrates cancellous bone CA, as shown in FIG. 8. As portion 156 is rotated, in the direction shown by arrow G, the external thread form configuration on surface 144 fixes portion 146 within cortical plate CL1 such that each fastener 130 is disposed in the first orientation. Rotating portion 156, in the direction shown by arrow GG, causes portion 146 to translate within sacrum S, in a direction shown by arrow HH, thus allowing for adjustment of portion 146 within cortical plate CL1.

Figure 9:
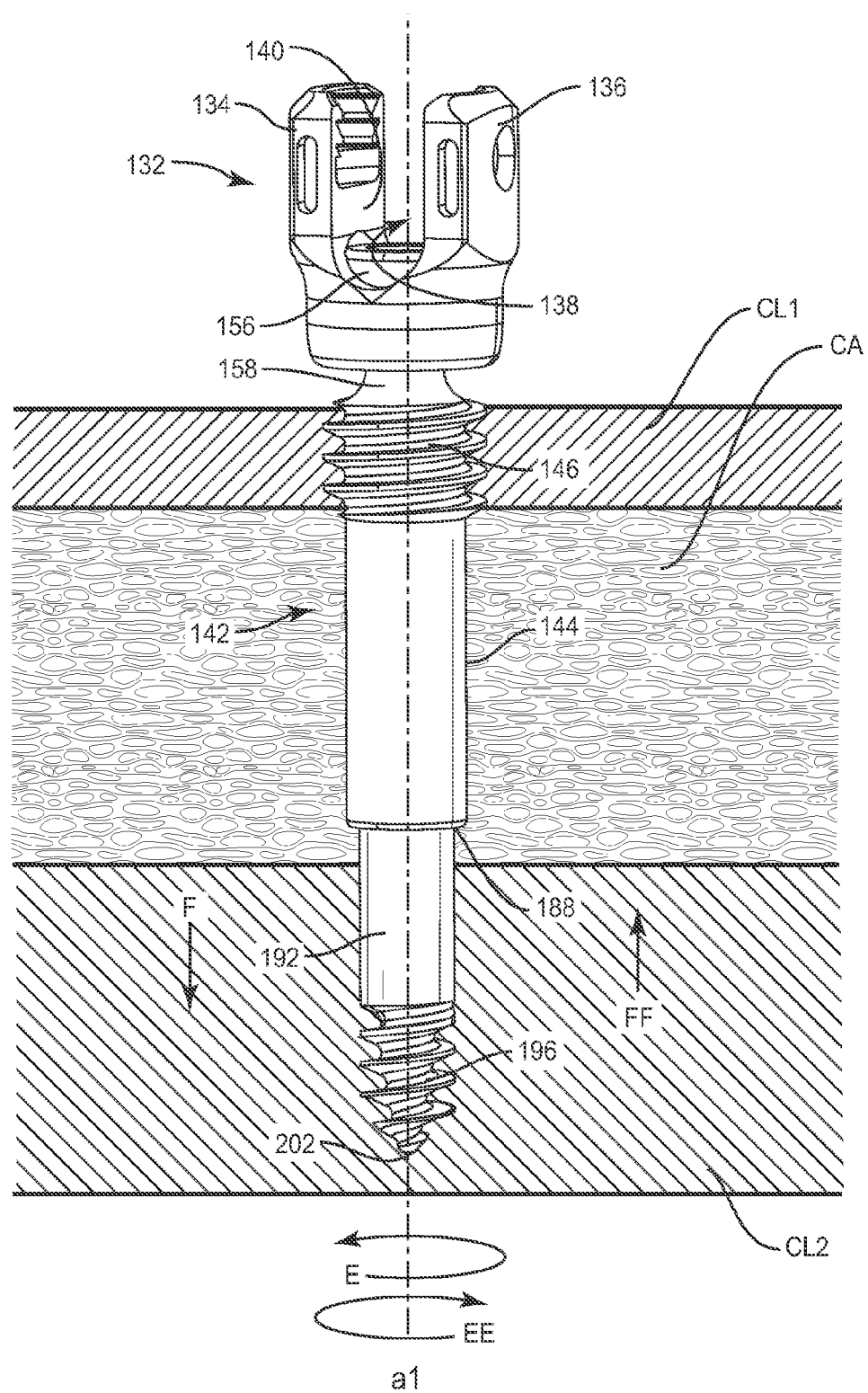
FIG. 9 is a perspective view, in part phantom, of the bone fastener shown in FIG. 6 disposed with tissue.

To expand each of fasteners 130 from the first orientation to the second orientation, a driver is passed through the axial passageway in portion 156 and passageway 165 and is engaged with socket 200. The driver rotates screw 190, in the direction shown by arrow E, such that screw 190 axially translates in sacrum S, in the direction shown by arrow F, such that the distance between tip 202 and face 188 increases. Screw 190 is rotated, in the direction shown by arrow E, such that tip 202 advances for penetration and fixation with cortical plate CL2, as shown in FIG. 9 and each of fasteners 130 are disposed in the second orientation.

To adjust the positioning of screws 190 within sacrum S according to the preference of a medical practitioner while fasteners 130 are in the second orientation, a driver is passed through the axial passageway in portion 156 of each fastener 130, passageway 165 and engaged with socket 200. The driver can rotate screw 190, in the direction shown by arrow E, such that screw 190 axially translates in sacrum S, in the direction shown by arrow F, or can rotate screw 190, in the direction shown by arrow EE, such that screw 190 axially translates in sacrum S, in the direction shown by arrow FF.

Receiver 132 is selectively and freely rotatable relative to end 142 such that a rod, such as, for example, rod 1150, may be moved within cavity 138. Cavity 138 is relatively rotatable to receive, engage and accommodate the orientation and position of rod 1150. A setscrew may be torqued and threaded with receiver 132 to securely attach rod 1150 with fastener 130. Each setscrew may be threaded into a threaded portion of surface 140 along arms 136, 138 such that the setscrew engages rod 1150, similar to that described. This configuration fixes fastener 130 in an orientation to prevent receiver 132 from moving relative to end 142 such that fastener 130 may receive and accommodate the orientation and position of rod 1150.

Figure 10:
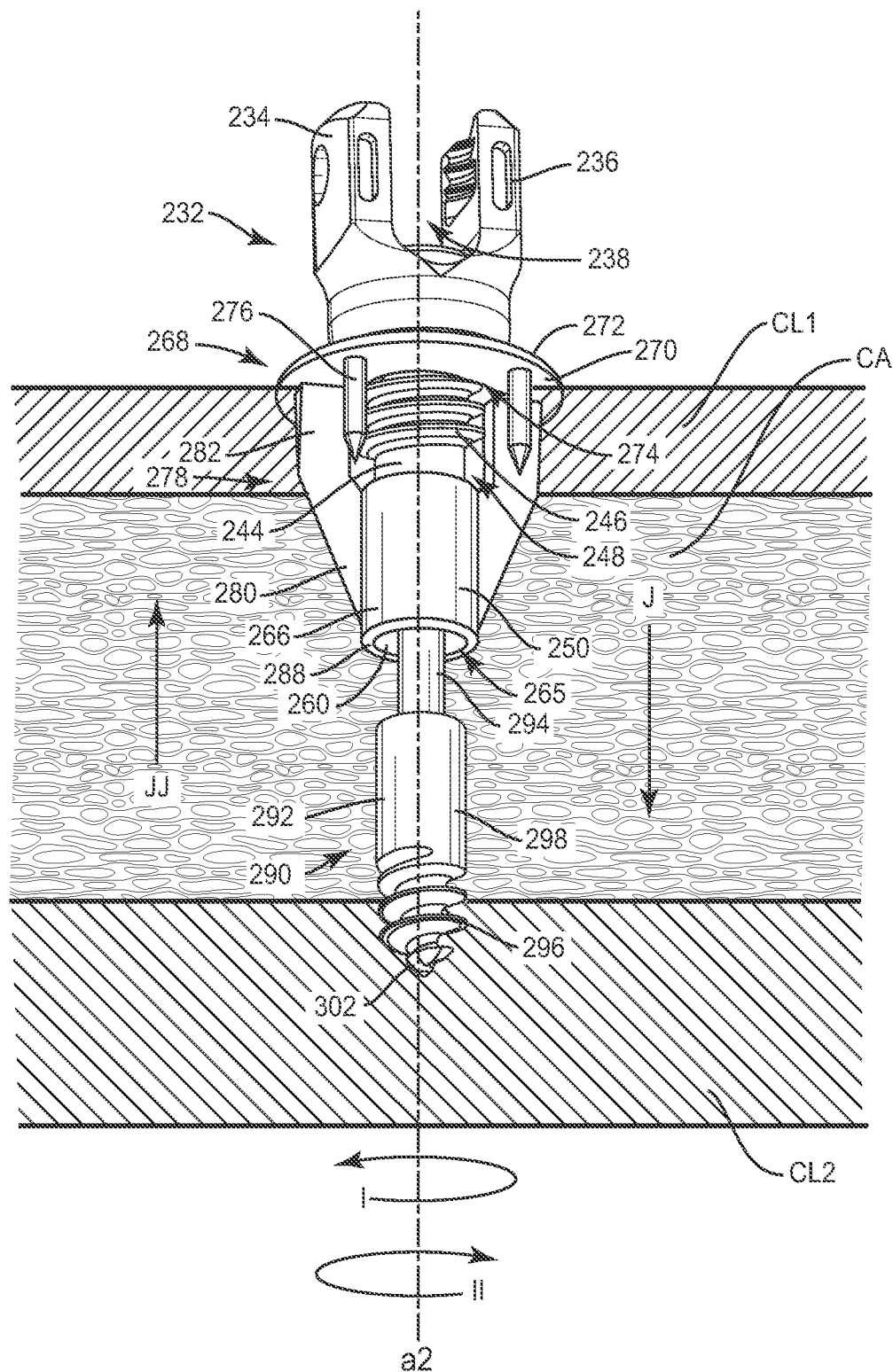
FIG. 10 is a perspective view of one particular embodiment of a bone fastener of a surgical system in accordance with the principles of the present disclosure disposed with tissue.
Figure 11:
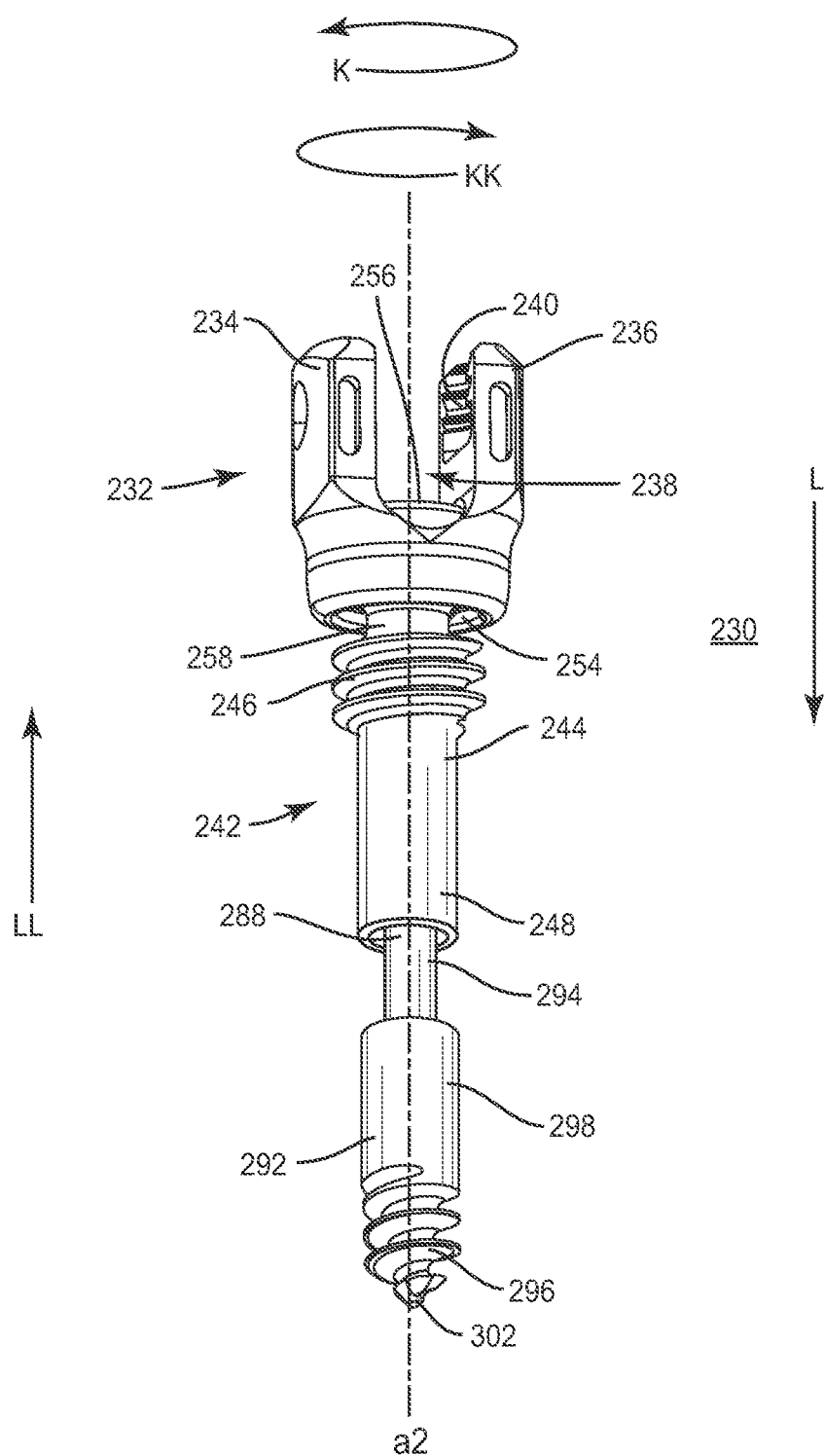
FIG. 11 is a perspective view of components of the bone fastener shown in FIG. 10.
Figure 12:
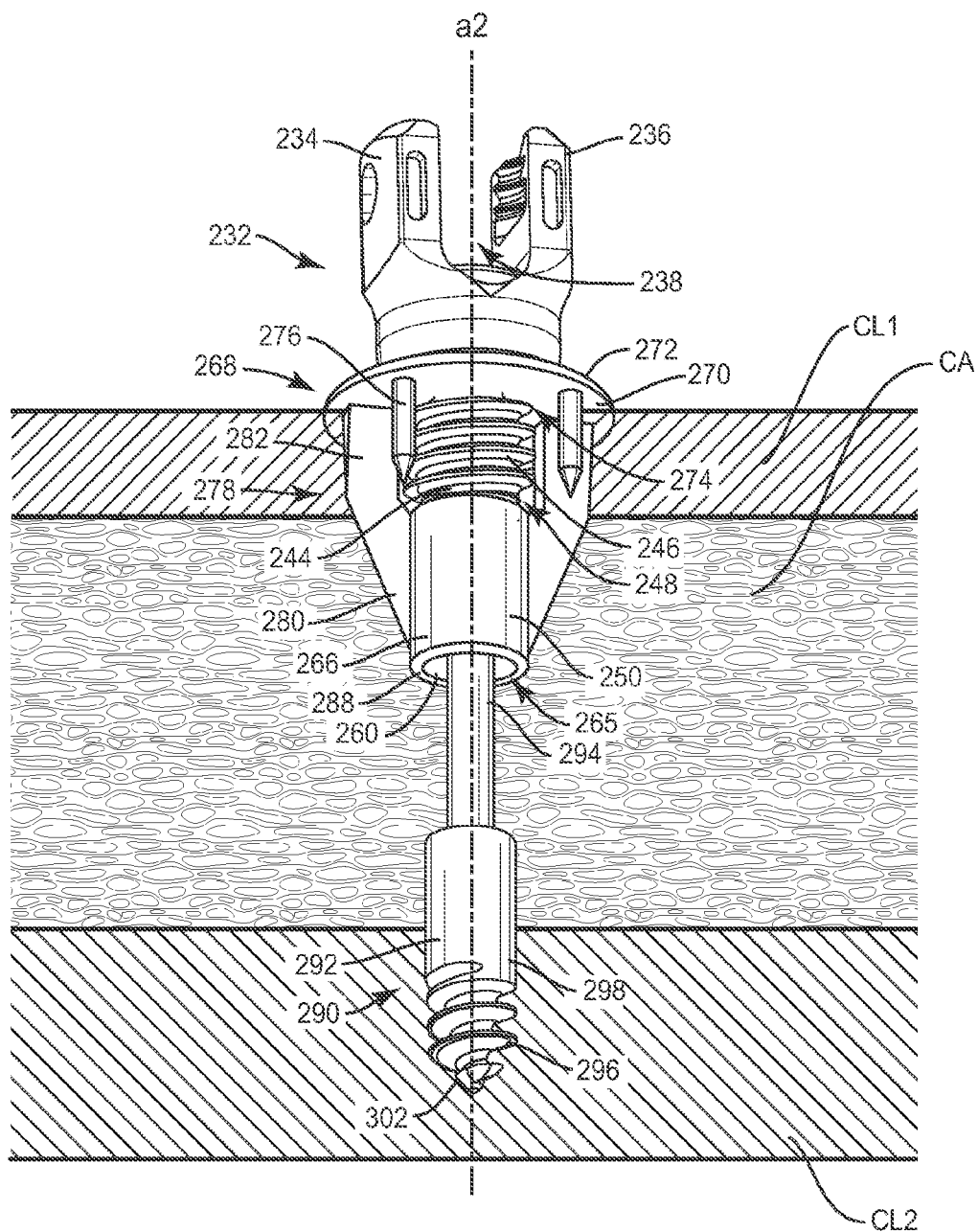
FIG. 12 is a perspective view of components of the bone fastener shown in FIG. 10 disposed with tissue.

In one embodiment, as shown in FIGS. 10-12, the surgical system includes a fastener 230, similar to the fasteners and methods described herein. Fastener 230 includes a receiver 232 defining a longitudinal axis a2 and including a pair of spaced apart arms 234, 236 that define an implant cavity 238 configured for disposal of a spinal rod, such as, for example rod 1150. Arms 234, 236 extend parallel to axis a2. Arms 234, 236 each include an arcuate outer surface having at least one recess or cavity configured to receive an insertion tool, compression instrument and/or instruments for inserting and tensioning fastener 230.

An inner surface 240 of receiver 232 defines cavity 238 and is concavely curved such that cavity 238 is substantially U-shaped. Surface 240 includes a thread form located adjacent arm 234 and a thread form located adjacent arm 236 each configured for engagement with a setscrew to retain a spinal rod within cavity 238.

Receiver 232 includes a first end 242 having an outer surface 244 defining a first threaded portion 246 configured for penetrating fixation with a first cortical surface, described below, and a second portion 248 configured to engage an intermediate member 250 to retain receiver 232 with member 250. Surface 244 is smooth and/or even along portion 248. Portion 248 includes a threaded inner surface defining a passageway configured for movable disposal of a screw 290. The thread form configuration along the inner surface of portion 248 is an internal or female thread form.

In one embodiment, end 242 and receiver 232 are monolithically formed and are not movable relative to one another. In one embodiment, receiver 232 includes an aperture 254 extending through surface 240 defining a passageway configured for disposal of end 242 to movably engage end 242 with receiver 232. End 242 includes a neck 258 positioned between portion 246 and portion 256 having a width that is less than the width of aperture 254. Neck 258 is concavely curved in a circumferential orientation and configured for disposal within aperture 254 such that receiver 232 is rotatable relative to end 242 through an angular range of 0-360 degrees in a plurality of planes, such as, for example, the sagittal, coronal or transverse plane of a body of a patient for alignment of receiver 232 with of a spinal rod such that the spinal rod may be disposed within cavity 238. Receiver 232 is rotatable to a selected angle through and within angular range relative to axis a2 in a plurality of planes that lie in a cone configuration, similar to that shown with regard to fastener 30 in FIG. 2.

In one embodiment, portion 256 includes a tool socket (not shown) defined within and/or recessed in a proximal face of portion 256. The tool socket is configured for disposal of a driver capable of rotating portion 256 in a first direction, such as, for example, clockwise, and a second direction, such as, for example, counterclockwise, about axis a2. It is envisioned that the tool socket in portion 256 may have a hexagonal or star-shaped configuration configured for disposal of a correspondingly shaped portion of a driver. In one embodiment, end 242 includes an axial passageway (not shown) extending through portions 256, 246, 248 along axis a2 configured for movable disposal of a driver, as will be described. It is envisioned that the axial passageway has a width that is less than a width of the tool socket in portion 256 such that the longitudinal passageway may extend through the tool socket. In one embodiment, portion 256 includes a first tool socket configured to facilitate rotation of portion 256 and the axial passageway has a smaller dimension than the first tool socket such that a driver may pass through the proximal and intermediate members and engage the distal member, as described.

Member 250 is configured for disposal within tissue, such as, for example, bone, and includes an inner surface 260 defining an axial passageway 265 configured for movable disposal of portion 248. Surface 260 is smooth and/or even and is configured to engage the smooth and/or even surface 244 along portion 248 to engage receiver 232 with member 250. Passageway 265 a width that is greater than or equal to a width of portion 248 such that surface 244 engages surface 260 when portion 248 is disposed within passageway 265 to permit axial translation of end 242 within passageway 265.

Member 250 includes an arcuate outer surface 266 that is smooth and/or even to prevent fastener member 250 from toggling during implantation of member 250 within tissue, for example. Member 250 includes a plate 268 having a first planar surface 270 configured to engage tissue and a second planar surface 272 configured to engage receiver 232. Plate 268 is substantially circular. Surface 270 includes at least one spike 276 extending therefrom. Surface 270 includes a plurality of spikes 276 extending therefrom and disposed radially about surface 270 in a circumferential orientation. Plate 268 has a height between surfaces 270, 272, which is substantially uniform such that plate 268 has a disc shaped configuration. Plate 268 defines an opening 274 extending through surfaces 270, 272 configured for disposal of end 242. Opening 274 is in communication with passageway 265. Opening 274 is substantially circular and has a width that is greater than a width of end 242 such that portions 246, 248 may be advanced distally through opening 274 along axis a2. The thread form configuration on surface 244 has a major diameter that is greater than the width of opening 274 and a minor diameter that is less than or equal to the width of opening 274 such that portion 246 may movably engage opening 274 to advance end 242 distally along axis a2 within opening 274 such that the thread form configuration on surface 244 is positioned below surface 270 to prevent end 242 from moving proximally along axis a2.

Surface 266 includes a pair of arms 78 extending therefrom and disposed radially about surface 266 in a circumferential orientation to connect plate 268 with member 250. Arms 278 include a first part 280 extending from surface 266 such that first part 280 is disposed at an acute angle relative to longitudinal axis a2 and a second part 282 extending between part 280 and surface 270 such that part 282 is parallel to axis a2.

Screw 290 includes an outer surface 292 extending between a proximal portion 294 and a second threaded portion 296 configured for penetrating fixation with a second cortical surface, as described. Portion 294 has a width that is less than a width of portion 296. The width of portion 296 is equivalent to a width of end 242 such that portion 296 and end 242 form a continuous outer surface when engaged with one another. Portion 294 includes an external thread form configuration (not shown) configured to engage the threads on the inner surface of portion 248 to engage screw 290 with end 242. Portion 296 is configured for penetrating fixation with a second cortical surface, as described. Screw 290 includes a pointed tip 302 at a distal end of portion 296. Screw 290 includes an inner surface defining a tool socket (not shown) extending into a proximal face of portion 294 along axis a2 that is in communication with the axial passageway extending through portion 156 and the passageway extending through portion 248 such that a tool, such as, for example, a driver may be advanced through receiver 232 and into the tool socket to facilitate penetrating fixation of screw 290 with tissue and/or adjust the position of screw 290 relative to end 242.

The thread form configuration on the outer surface of portion 294 engages the thread form configuration on the inner surface of portion 248 to facilitate axial translation of screw 290 relative to receiver 232. Screw 290 may be rotated a first direction, such as, for example, clockwise, as shown by arrow I in FIG. 10, and a second direction, opposite the first direction, such as, for example, a counterclockwise direction as shown by arrow II, relative to receiver 232 such that screw 290 telescopes within the passageway defined by the inner surface of portion 248 to facilitate axial translation of screw 290 relative to receiver 232. For example, rotating screw 290, in the direction shown by arrow I, causes screw 290 to axially translate within the passageway defined by the inner surface of portion 248, in the direction shown by arrow J. For example, rotating screw 290, in the direction shown by arrow II, causes screw 290 to axially translate within the passageway defined by the inner surface of portion 248, in the direction shown by arrow JJ.

Screw 290 includes an unthreaded portion 298 between portions 294, 296 such that the thread form configurations on surface 292 along portion 294 and portion 296 are non-continuous. The external thread form configuration on surface 292 along portion 294 has a major diameter that is greater than the width of the passageway defined by the inner surface of portion 248 and a minor diameter that is less than or equal to the width of the passageway defined by the inner surface of portion 248 such that surface 292 engages the inner surface of portion 248 when portion 294 is disposed within passageway 265 to prevent lateral movement of screw 290 within passageway 265 when portion 294 is disposed within passageway 265.

In one embodiment, the system including fastener 230 is attached to sacrum S for a surgical arthrodesis procedure, such as a fusion of the affected section of the spine, such as, for example, the sacroiliac joint, to facilitate healing and therapeutic treatment. In one embodiment, the system including fastener 230 is attached to vertebrae V, sacrum S and/or ilium I for a dynamic stabilization application.

Receiver 232 and screw 290 are axially translatable relative to one another such that fastener 230 is expandable between a first orientation such that one of portion 246 and portion 296 is engaged with a respective cortical surface, such as, for example, plate CL1 or plate CL2 of sacrum S and a second orientation such that the other of portion 246 and portion 296 is engaged with its respective cortical surface.

To dispose fastener 230 into the first orientation, pilot holes are made in sacrum S corresponding to each fastener 230 for receiving members 250. Members 250 are inserted or otherwise connected to sacrum S according to the particular requirements of the surgical treatment. Each of members 250 are advanced distally along axis a2 into sacrum S until surfaces 270 engage plate CL1. Surface 270 includes bone penetrating elements extending therefrom. The bone penetrating elements are driven for fixation into sacrum S. It is envisioned that member 250 may be advanced into sacrum S until surface 270 is flush with an outer surface of plate CL1.

Receiver 232 is engaged with screw 290 such that receiver 232 can engage member 250 with screw 290 attached to receiver 232 to connect receiver 232 and screw 290 with member 250. To engage receiver 232 with member 250, portion 294 is positioned relative to portion 248 such that the threads on surface 292 along portion 294 is aligned with the threads in the passageways defined by the inner surfaces of portion 248. A driver is inserted through the axial passageway in portion 256 and into the tool socket in the proximal face of screw 290. The driver is rotated, in the direction shown by arrow II, to translate screw 290 within the passageways defined by the inner surfaces of portion 248, in the direction shown by arrow JJ, such that the distance between tip 302 and distal face 288 of end 242 decreases. Rotation of the driver, in the direction shown by arrow I, causes screw 290 to translate within the passageways defined by the inner surfaces of portion 248, in the direction shown by arrow J, such that the distance between tip 302 and face 288 increases.

Receiver 232 and screw 290 is inserted through opening 274 and into passageway 265 such that surface 244 engages surface 260. A driver is inserted into the tool socket in the proximal face of portion 256. The driver is rotated in a first direction, such as, for example, a clockwise direction as shown by arrow K in FIG. 11, such that portion 246 axially translates within sacrum S, in the direction shown by arrow L, and the external thread form configuration on portion 246 movably engages aperture 274 and/or surfaces of plate CL1, as shown in FIG. 10. The driver is rotated, in the direction shown by arrow K in FIG. 11, until the external thread form configuration on portion 246 engages aperture 274. The driver is further rotated, in the direction shown by arrow K, until the thread form configuration on portion 248 is positioned below surface 270 such that the thread form configuration on portion 248 engages plate CL1 to fix portion 246 within sacrum S, as shown in FIG. 10. Portion 296 is fixed within cancellous bone CA such that fasteners 230 are disposed in the first orientation. Receivers 232 are disposed relative to plate CL1 and may be adjusted by rotating the driver, in the direction shown by arrow KK, to axially translate end 242 of receiver 232 within apertures 274 and/or sacrum S in the direction shown by arrow LL.

To expand fasteners 230 from the first orientation to the second orientation, a driver is inserted through the apertures in portions 256 and the passageways in portions 248 and into the tool sockets in the proximal faces of screws 290. The driver is rotated, in the direction shown by arrow I, to axially translate screws 290 within sacrum S, in the direction shown by arrow J. The driver is rotated, in the direction shown by arrow I, until portions 296 are fixed in plate CL2 and fasteners 230 are disposed in the second orientation, as shown in FIG. 12.

Receivers 232 are selectively and freely rotatable relative to ends 242 such that rods 1150 (FIG. 5) may be oriented within cavities 238 by sliding the rods within cavities 238. According to the orientation and position of rod 1150, fasteners 230 are independently and selectively positioned such that each cavity 238 is selectively rotatable relative to end 242. Cavity 238 is relatively rotatable to receive, engage and accommodate the orientation and position of each rod 1150.

Setscrews may be torqued and threaded with each receiver 232 to securely attach rods 1150 with sacrum S. Each setscrew may be threaded into a threaded portion of an inner surface of arms 236, 238 such that the setscrew engages rod 1150. As the setscrew is threaded into arms 236, 238, the setscrew applies a force to rod 1150 disposed with cavity 238. This force is transmitted through rod 1150 such that rod 1150 engages the surfaces that define cavity 238 causing at least a portion of receiver 232 to engage plate 268. This configuration fixes fastener 230 in an orientation to prevent receiver 232 from moving relative to end 242 such that fastener 230 may receive and accommodate the orientation and position of each rod 1150.

The fasteners of the surgical system described herein may be employed as a bone screw, pedicle screw, mono-axial screw or multi-axial screw used in spinal surgery. It is contemplated that the components of the surgical system may be coated with an osteoconductive material such as hydroxyapatite and/or osteoinductive agent such as a bone morphogenic protein for enhanced bony fixation. It is further contemplated that components of the surgical system may be coated with therapeutic and/or pharmacological agents for release, including sustained release, to treat, for example, pain, inflammation and degeneration. The fasteners can be made of radiolucent materials such as polymers. Radiomarkers may be included for identification under x-ray, fluoroscopy, CT, or other imaging techniques. Metallic or ceramic radiomarkers, such as tantalum beads, tantalum pins, titanium pins, titanium endcaps, and platinum wires can be used.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
   a proximal member including an inner surface that defines an implant cavity and an outer surface including a first threaded portion configured for penetrating fixation with tissue and a second portion, the proximal member defining a longitudinal axis;
   an intermediate member including an inner surface extending between a proximal portion connected with the second portion and a distal portion, the proximal portion of the intermediate member including a plate having a first surface configured to engage tissue and a second surface, the plate defining an opening configured for disposal of the proximal member; and
   a distal member including an outer surface extending between a proximal portion disposed with the distal portion of the intermediate member and a distal portion configured for penetrating fixation with tissue, the distal member being configured for axial translation relative to the intermediate member.

2. A bone fastener as recited in claim 1, wherein the first threaded portion defines a first thread form and the second portion defines a second thread form.

3. A bone fastener as recited in claim 1, wherein the inner surface of the intermediate member is threaded for engagement with the second portion of the proximal member.

4. A bone fastener as recited in claim 1, wherein the first surface includes a plurality of spikes extending therefrom.

5. A bone fastener as recited in claim 1, wherein the proximal portion of the intermediate member includes a pair of spaced apart arms extending to the plate.

6. A bone fastener as recited in claim 1, further comprising a spacer configured for threaded engagement with the inner surface of the intermediate member.

7. A bone fastener as recited in claim 1, wherein the inner surface of the intermediate member is threaded for engagement with the proximal portion of the distal member.

8. A bone fastener as recited in claim 1, wherein the proximal portion of the distal member slidably engages the inner surface of the intermediate member to facilitate axial translation of the distal member relative to the intermediate member.

9. A bone fastener as recited in claim 1, wherein the second portion of the proximal member is fixed with the inner surface of the intermediate member and the proximal portion of the distal member slidably engages an inner surface of the second portion of the proximal member to facilitate axial translation of the distal member relative to the intermediate member.

10. A bone fastener as recited in claim 1, wherein the second portion of the proximal member is monolithically formed with the intermediate member and the proximal portion of the distal member is threaded for engagement with the inner surface of the intermediate member.

11. A bone fastener as recited in claim 1, wherein the members are disposed in a coaxial orientation.

12. A bone fastener as recited in claim 1, wherein the proximal member and the intermediate member define an axial passageway disposed in communication with the proximal portion of the distal member, the proximal portion of the distal member defining a tool socket.

13. A bone fastener comprising:
   a receiver including a pair of spaced apart arms that define an implant cavity configured for disposal of a spinal rod, the receiver further including an outer surface including a first threaded portion configured for penetrating fixation with a first cortical layer and a second portion, the receiver defining a longitudinal axis;
   an intermediate member including an inner surface extending between a proximal portion connected with the second portion and a distal portion, the proximal portion of the intermediate member including a plate having a first surface configured to engage tissue and a second surface, the plate defining an opening configured for disposal of the receiver; and
   a screw including an outer surface extending between a proximal portion disposed with the distal portion of the intermediate member and a second threaded portion configured for penetrating fixation with a second cortical layer,
   wherein one of the receiver and the screw is axially translatable relative to the intermediate member such that the bone fastener is expandable between a first orientation such that one of the first threaded portion and the second threaded portion is engaged with a respective cortical layer and a second orientation such that the other of the threaded portions is engaged with its respective cortical layer.

14. A bone fastener as recited in claim 13, wherein the screw is configured to telescope within the inner surface of the intermediate member to facilitate axial translation of the screw relative to the intermediate member.

15. A bone fastener as recited in claim 13, wherein the receiver or the screw are threaded and rotatable relative to the intermediate member to facilitate axial translation of the receiver or the screw relative to the intermediate member.

16. A method for treating a spine, the method comprising the steps of:
   providing a bone fastener comprising:
      a proximal member including an inner surface that defines an implant cavity and an outer surface including a first threaded portion and a second portion, the proximal member defining a longitudinal axis,
      an intermediate member including an inner surface extending between a proximal portion connected with the second portion and a distal portion, and
      a distal member including an outer surface extending between a proximal portion disposed with the distal portion of the intermediate member and a distal portion having a second threaded portion;
   fastening the first threaded portion with a first cortical layer or the second threaded portion with a second cortical layer to dispose the bone fastener in a first orientation;
   translating one of the proximal member and the distal member relative to the intermediate member to expand the bone fastener; and
   fastening the other of the threaded portions with a respective cortical layer to dispose the bone fastener in a second orientation.

17. A method as recited in claim 16, wherein the step of translating includes rotating the proximal member to facilitate axial translation of the proximal member relative to the intermediate member.

18. A method as recited in claim 16, wherein the step of translating includes rotating the distal member to facilitate axial translation of the distal member relative to the intermediate member.

* * * * *